United States Patent [19]
Holden et al.

[11] Patent Number: 4,747,972
[45] Date of Patent: May 31, 1988

[54] SULFONIC ACID COMPOSITIONS HAVING REDUCED SULFUR-CONTAINING CONTAMINANTS

[75] Inventors: Thomas F. Holden, Mentor; Albert F. Baumann, Highland Heights, both of Ohio

[73] Assignee: The Lubrizol Corporation, Whickliffe, Ohio

[21] Appl. No.: 38,390

[22] Filed: Apr. 15, 1987

Related U.S. Application Data

[62] Division of Ser. No. 622,921, Jun. 21, 1984, Pat. No. 4,677,074.

[51] Int. Cl.$^4$ .................. C10M 105/72; C07B 45/02
[52] U.S. Cl. ...................... 252/33.2; 252/33; 252/353; 252/549; 44/51; 260/503; 260/504 R
[58] Field of Search ............. 252/33.2, 33, 353, 549, 252/550, 554, 558; 44/51; 260/399, 503, 400; 423/544, 545, 549

[56] References Cited

U.S. PATENT DOCUMENTS

| | | | |
|---|---|---|---|
| 2,848,415 | 8/1958 | Logan | 252/33 |
| 3,126,340 | 3/1964 | Sabol | 252/33 |
| 3,242,080 | 3/1966 | Wiley et al. | 252/33 |
| 3,320,162 | 5/1967 | Axe | 252/33 |
| 3,524,814 | 8/1970 | Sabol | 252/33.2 |
| 3,609,076 | 9/1971 | Sabol | 252/33.2 |
| 3,865,737 | 2/1975 | Kemp | 252/33 |
| 4,148,740 | 4/1979 | Cease | 252/33.2 |
| 4,206,062 | 6/1980 | Derbyshire | 252/33.2 |
| 4,225,446 | 9/1980 | Arnold | 252/33.2 |
| 4,306,983 | 12/1981 | Allian | 252/33.2 |
| 4,677,074 | 6/1987 | Holden | 423/541 |

FOREIGN PATENT DOCUMENTS

| | | | |
|---|---|---|---|
| 0723147 | 12/1965 | Canada | 252/33.2 |
| 2058118 | 4/1981 | United Kingdom | 252/32 |

*Primary Examiner*—William R. Dixon, Jr.
*Assistant Examiner*—James M. Hunter, Jr.
*Attorney, Agent, or Firm*—Karl Bozicevic; Denis A. Polyn; Robert A. Franks

[57] ABSTRACT

Processes of reducing the inorganic sulfur-containing acid and the low equivalent weight organic sulfonic acid content of an acid mass comprising organic sulfonic components and inorganic sulfonating agent contaminants are described. In general, the process comprises the steps of (a) treating the acid mass with ammonia in the presence of water to neutralize the acids in said acid mass and to form a mixture containing the ammonium salts of said acids, (b) allowing separation of the mixture to provide a lower aqueous phase containing water-soluble ammonium salts and an upper phase comprising the oleophilic alcohol and ammonium salts of the organic sulfonic acids, and (c) recovering at least a portion of said upper phase. The efficiency of the reduction of undesirable materials from the acid mass can be increased by subjecting the recovered upper phase to additional water extractions in the presence of the oleophilic alcohol.

The ammonium salts of the organic sulfonic acids recovered by the above process can be converted to oil-soluble metal salts by reacting said ammonium salts with a basically reacting metal compound in such amounts and under such conditions as to form metal salts of said organic sulfonic acids. The metals salts prepared in this manner may be neutral metal salts or highly basic metal salts. The neutral and metal basic salts are useful in a variety of applications including lubricants and fuels.

12 Claims, No Drawings

SULFONIC ACID COMPOSITIONS HAVING REDUCED SULFUR-CONTAINING CONTAMINANTS

CROSS REFERENCES

This is a division of application Ser. No. 622,921 filed June 21, 1984 which is now U.S. Pat. No. 4,677,074 issued June 30, 1987.

FIELD OF THE INVENTION

This invention relates to processes of reducing the inorganic sulfur-containing acid and the low equivalent weight organic sulfonic acid content of an acid mass comprising organic sulfonic acid components and inorganic sulfonating agent acid contaminants. More particularly, the processes involve the utility of water, ammonia and oleophilic alcohols in effecting the reduction. The invention also relates to the conversion of ammonia salts prepared in accordance with the above process of the invention to useful metal salts which may be neutral metal salts or highly basic metal salts of sulfonic acids. Such metal salts are useful particularly as additives in lubricating oils and normally liquid fuels.

BACKGROUND OF THE INVENTION

It is well known that hydrocarbon sulfonates such as petroleum sulfonates are useful in a wide variety of applications, particularly in the preparation of compounds and compositions which are useful as additives in lubricants and normally liquid fuels. Procedures for preparing such sulfonates have been described extensively in the prior art. The economically feasible methods of preparing metal salts of organic sulfonic acids include the steps of reacting organic compounds with a sulfonating agent, separating undesired components (acid sludge) from the sulfonated product, and thereafter treating the sulfonated product with a metal base to form metal salts. The sulfonation may be carried out with a variety of sulfonating agents such as sulfuric acid, chlorosulfonic acid, oleum, or sulfur trioxide. In spite of the removal of the acid sludge after sulfonation, the sulfonated product mixture resulting from the sulfonation of the organic compound still contains appreciable amounts of unchanged inorganic sulfonating agent and organic contaminants such as low equivalent weight organic sulfonic acid components.

The removal of the inorganic sulfonating agents from the sulfonated acid masses has been the subject of much study and often has involved expensive and inconvenient operating procedures. One of the difficulties resides in the mutual solubility characteristics of the sulfonated product and its salts with the inorganic acid contaminant and their salts. Another difficulty arises from the ability of the metal salts, especially the polyvalent metal salts, of the sulfonated products to act as dispersants for the metal salts of the inorganic acid contaminants and maintain the latter in suspension. The result often is a hazy solution which is unsuitable for many purposes.

The extraction of the inorganic contaminants (e.g., unreacted sulfonating agent) with aqueous solutions is not a complete solution to the problem since some of the water containing sulfuric acid remains dispersed in the product even after such extractions in the form of an aqueous emulsion. The sulfuric acid content will vary depending on the various processes utilized, but may be as high as 10-15% of the total weight of sulfonic acids and sulfuric acid.

The presence of sulfuric acid in the organic acid mass, even at low concentrations, is detrimental for many of the intended uses of the organic sulfonic acids. For example, when these organic sulfonic acids are neutralized with an alkali to prepare emulsifying compositions or rust-preventing compounds, the presence of an alkali metal sulfate may impair the emulsifying power of the organic sulfonate and even promote corrosion. When said acids containing minor amounts of sulfuric acid are neutralized with alkaline earth metal bases in order to prepare detergent additive oils, the impurity forms highly dispersed alkaline earth metal sulfates which makes the filtration of these additives difficult and decreases their dispersant power.

Several processes have been suggested in the prior art for reducing the inorganic sulfonating agent components in the sulfonated products, but many of these processes have not satisfactorily solved the problems. Processes have been suggested based on water extraction using oxygenated solvents, several successive extractions and at least one evaporation of the solvent. U.S. Pat. No. 4,087,456 describes a process for the production of hydrocarbon sulfonates involving the removal of undesired inorganic sulfites and sulfates and undesired hydrophylic hydrocarbon sulfonates utilizing combinations of inorganic hydroxides, water and neutral oleophilic organic compounds. Examples of the useful oleophilic organic compounds include alcohols such as pentanols, hexanols and octanols; alkyl phenols and cresols; aldehydes such as heptaldehyde; ketones such as cyclohexanone; esters such as butylbutyrate; and mixtures thereof. More specifically, the process involves adding to the sulfonated product mixture after neutralization with an inorganic hydroxide, from about 0.05 to about 10 moles of a neutral oleophilic organic compound and from 5 to about 500 moles of water, per mole of sulfonate groups in said product mixtures. U.S. Pat. No. 2,453,690 describes a process of producing polyvalent metal hydrocarbon sulfonates wherein water-soluble sulfonates ordinarily present in such mixtures are eliminated by diluting the batch of sulfonates undergoing metathesis or purification with a small amount, e.g., about 0.2 to 10% of a water-insoluble oil-soluble aliphatic alcohol or other oxygenated bearing organic solvent. Examples of such alcohols disclosed include amyl alcohol and butyl alcohol. Such alcohols are reported to be useful as emulsion-breaking liquids. Examples of other patents which describe the use of various oxygenated solvents in facilitating the purification of hydrocarbon sulfonic acid mixtures include U.S. Pat. Nos. 2,453,690; 2,924,617; 1,930,488; 2,168,315; 2,848,415; 3,242,080; 4,119,661; 4,177,208; and 2,739,982.

Processes for purifying organic sulfonic acid mixtures based on the precipitation of insoluble salts generally require longer reaction times and may give rise to difficulties relating to the separation of the precipitate which can be extremely fine. Also, such processes generally require the use of filtration procedures which can be time-consuming and expensive. U.S. Pat. No. 2,760,970 describes a process for the preparation of substantially pure metal salts of organic sulfonic acids wherein the inorganic sulfonating acid contaminants are removed as ammonium salt crystals. More specifically, the process involves treating a sulfonated acid mass containing the desirable organic sulfonic acid components and undesirable inorganic sulfonating agent acid contaminants with substantially anhydrous ammonia to neutralize at least substantially all of the inorganic sulfonating agent acid contaminant present, but less than 75% of the organic sulfonic acids to form as a solid phase, the ammonia derivative of said inorganic sulfonating agent contaminants. The solid contaminants are separated from the organic components, and the organic components are thereafter converted to desirable and useful metal salts of the organic components. U.S. Pat. No. 3,720,707 also describes a process for reducing the sulfuric acid content of alkyl aryl sulfonic acids by treating said sulfonic acids with ammonia or an ammonium salt in a quantity to form crystalline ammonium acid sulfate which is separated such as by filtration.

The preparation of useful polyvalent metal sulfonates involves, in general, a double decomposition reaction of an alkali metal or ammonium sulfonate with a particular polyvalent metal compound. When crude sulfonated acid masses are utilized in the double decomposition reaction, many undesirable side reactions occur, and it is often difficult to separate the organic and inorganic salts in the resulting mixture because the polyvalent metal sulfonates disperse the undesirable polyvalent metal sulfates. The result is a hazy solution which cannot be clarified conveniently or is a very viscous solution which must be subjected to additional treatment before it is satisfactory for many uses. Consequently, it is frequently preferable to utilize more expensive organic sulfonic acid mixtures which contain fewer impurities, or it is necessary to purify commercially available organic sulfonic acid mixtures before converting said mixtures to the more useful metal salts. It also has been discovered that neutral and alkaline metal sulfonates exhibiting improved properties can be obtained when the amount of low equivalent weight organic sulfonic acid present in the starting acid mass is reduced. Generally, the lower equivalent weight organic sulfonic acids are polysulfonic acids such as disulfonic and trisulfonic acids. Thus, a procedure which is effective in removing both the inorganic contaminants and the undesirable low equivalent weight organic sulfonic acids from the starting acid mass is desirable.

SUMMARY OF THE INVENTION

This invention relates to processes of reducing the inorganic sulfur-containing acid and the low equivalent weight organic sulfonic acid content of sulfonic acid mixtures. In general, the process comprises the steps of
(a) treating an acid mass with ammonia in the presence of water to neutralize the acids in said acid mass and form a mixture containing the ammonium salts of said acids,
(b) allowing separation of the mixture to provide a lower aqueous phase containing water-soluble ammonium salts and an upper phase comprising the oleophilic alcohol and ammonium salts of the organic sulfonic acids, and
(c) recovering at least a portion of said upper phase.
The upper phase recovered in accordance with the above process contains reduced amounts of inorganic sulfonating agent acid contaminants. The amount of such contaminants, as well as any low equivalent weight organic sulfonic acid components present in the recovered phase can be further reduced by additional extractions with water. It has been discovered that whereas the first extraction removes primarily inorganic salts, subsequent extractions with water result in the removal of additional inorganic salts as well as the undesirable low equivalent weight organic sulfonic acids.

The conversion of such recovered ammonium salts to useful metal salts of the organic sulfonic acids is described as well as the use of such metal salts in lubricants and normally liquid fuels.

DESCRIPTION OF THE INVENTION

As mentioned above, the invention relates to processes for reducing the inorganic sulfur-containing acid and the low equivalent weight organic sulfonic acid content of an acid mass which comprises organic sulfonic acid components and inorganic sulfonic acid contaminants. The acid masses which can be improved in accordance with the process of this invention are organic sulfonic acid compositions which can be prepared by a variety of techniques, and many such organic sulfonic acid compositions are available commercially. The sulfonic acid compositions are prepared by contacting at least one organic compound with a sulfonating agent under conditions so as to form the desired organic sulfonic acid.

The sulfonation of many organic compounds to form organic sulfonic acids has been described in the prior art. Generally, the organic compound should be a sulfonatable organic compound substantially free from any reactive substituents or contaminants which would prevent the normal sulfonation reaction from occurring. Such sulfonatable compounds should in most cases possess at least one replaceable hydrogen atom, and preferably such compounds are hydrocarbon compounds.

Suitable sulfonatable organic compounds include aromatic compounds having at least one resonant ring structure and having a replaceable hydrogen atom attachment to a nuclear carbon atom. Especially preferred are aromatic hydrocarbon compounds.

By the term aromatic hydrocarbon, as used in the specification and appended claims, is meant hydrocarbon compounds containing at least one resonant ring structure. More specifically it refers to benzene, biphenyl, naphthalene, anthracene, phenanthrene, and their aliphatic hydrocarbon substituted derivatives. Suitable examples include benzene, toluene, xylene, methylethyl benzene, diethyl benzene, biphenyl, naphthalene, and the alkyl and cycloalkyl substitution products of these, such as, diisobutyl-substituted benzene, disobutyl-substituted toluene, wax-substituted benzene, nonyl benzene, polydodecyl benzene, polydodecyl toluene, polydodecyl naphthalene, terpene-substituted benzene, kerosene-substituted benzene, aromatic extracts or fractions of petroleum, e.g., solvent-extracted petroleum oil, preferably having a boiling point greater than 250° F., etc. Preference is given the aliphatic hydrocarbon-substituted benzenoid hydrocarbons in which the aliphatic hydrocarbon groups contain a total of from 1 to 60 carbon atoms, and special preference is given to those in which the aliphatic hydrocarbon groups contain a total of from 8 to 40 carbon atoms.

Olefins, particularly long-chain olefins which have been sulfonated into sulfonic acids also can be treated in accordance with the process of the present invention. Examples of acid masses prepared by the sulfonation of an olefin or an olefin mixture are described in, for example, U.S. Pat. Nos. 2,094,451; 2,187,244; and 3,376,336.

Suitable sulfonation agents include sulfuric acid, oleum, sulfur trioxide, or chlorosulfonic acid. Preference is given to concentrated sulfuric acid, oleum, and sulfur trioxide, with special preference given to sulfur trioxide. Advantageous results are obtained using oleum as the source of gaseous sulfur trioxide.

The temperature of sulfonation steps may vary within the range from about −20° C. to about 100° C. or higher. Ordinarily it is desirable to carry out the sulfonation process within the range from about 25° C. to about 75° C., since lower temperatures tend to retard sulfonation and higher temperatures do not afford any outstanding advantages and tend to cause cleavage of long chain alkyl groups and effect oxidation and partial polymerization of olefinic fragments resulting from such cleavage.

The reaction periods for sulfonation range from about a few seconds to about 60 minutes or more. Generally about 15 to 20 minutes are sufficient to effect complete sulfonation per a charge of sulfonating agent. It will be realized, however, that the sulfonation time will depend to a certain extent on the technique utilized and on the amount and type of material being sulfonated.

It may be desirable in some instances to perform the sulfonation step in the presence of about 1.5 volumes of a low boiling diluent, such as n-butane, per volume aromatic hydrocarbon. Rises in temperature resulting from sulfonation vaporizes a portion of such diluent, and the resulting cooling effect tends to maintain the reaction temperature at a constant level, thereby eliminating local high temperatures in the reaction vessel. The diluent may be removed later by vaporization.

Upon allowing the reaction mixture to stand after sulfonation of the organic compounds, the mixture separates into an upper organic sulfonic acid layer and a lower acid sludge layer. If the organic compound is a petroleum fraction the upper layer contains mahogany sulfonic acids and the lower layer may contain green sulfonic acids.

It may be desirable to separate the acid sludge layer from the sulfonic acids prior to ammonia treatment in accordance with this invention. In the batch process, if successive charges of a sulfonating agent are used, it may be desirable to remove the acid sludge layer after each charge. In the continuous type operation the reaction mass is transferred to a settling tank for sufficient time to allow settling of the acid sludge layer.

It should be understood that the above sludge separation step prior to ammonia treatment is optional and in some instances may be desirably omitted. Ordinarily, however, it is preferred to remove the acid sludge before ammonia treatment, since this method economizes the use of ammonia and provides a more satisfactory product for certain uses, such as a motor oil dispersant and detergent. Furthermore, the acid sludge can be treated to restore its sulfonating properties and can be reused in the sulfonation process.

Among the sulfonic acids which can be treated in accordance with the invention are the following: mahogany sulfonic acid; petroleum sulfonic acids; mono- and polywax substituted naphthalene sulfonic, phenol sulfonic, diphenyl ether sulfonic, diphenyl ether disulfonic, naphthalene, disulfide sulfonic, naphthalene disulfide disulfonic, diphenyl amine disulfonic, diphenyl amine sulfonic, thiophene sulfonic, alphachloronaphthalene sulfonic acids, etc.; other substituted sulfonic acids such as cetyl chloro-benzene sulfonic acids, cetyl-phenol sulfonic acids, cetyl-phenol disulfide sulfonic acids, cetyl-phenol mono-sulfide sulfonic acids, cetyl caprylbenzene sulfonic acids, di-cetyl thianthrene sulfonic acids, di-lauryl beta-naphthanol sulfonic acids, and dicapryl nitronaphthalene sulfonic acids; aliphatic sulfonic acids such as paraffin wax sulfonic acids, unsaturated paraffin wax sulfonic acids, hydroxy substituted paraffin wax sulfonic acids, tetraisobutylene sulfonic acids, tetraamylene sulfonic acids, chloro-substituted paraffin wax sulfonic acids, nitroso paraffin wax sulfonic acids, etc.; cycloaliphatic sulfonic acids, such as petroleum naphthene sulfonic acids, cetyl-cyclopentyl sulfonic acids, lauryl-cyclo-hexyl sulfonic acids, bis-(diisobutyl)-cyclohexyl sulfonic acids, mono- and polywax substituted cyclohexyl sulfonic acids, etc.

As used herein, the terminology "petroleum sulfonic acids" or "petrosulfonic acids" is intended to cover that well-known class of sulfonic acids derived from petroleum products according to conventional processes such as disclosed in U.S. Pat. Nos. 2,480,638; 2,483,800; 2,717,265; 2,726,261; 2,794,829; 2,832,801; 3,225,086; 3,337,613; 3,351,655; and the like. Sulfonic acids also are discussed in prior U.S. patents as Nos. 2,616,904; 2,616,905; 2,723,234; 2,723,235; 2,723,236; 2,777,874; and the other U.S. patents referred to in each of these patents. Thus it is seen that the oil-soluble sulfonic acids treated in accordance with the invention are well-known in the art and require no further discussion herein.

Illustrative of more specific sulfonic acids which can be treated in accordance with the process of the invention are the oil-soluble petroleum sulfonic acids such as the "mahogany acids" of about 300 to 800 molecular weight, dilaurylaryl sulfonic acid, lauryl cetyl aryl sulfonic acid, alkylated benzene sulfonic acids, wherein the aromatic content of the mixture comprises from 25–30% of the sulfonatable portion of the feedstock and wherein the molecular weight of said aromatic content is in the range of from about 250 to 900. Bright stock is the relatively viscous petroleum fraction obtained by dewaxing and treatment with, e.g., fuller's earth, of the distillation residue after the volatile petroleum fractions have been separated. It usually has a viscosity value of at least about 80 SUS (Saybolt Universal Seconds) at 210° F., more often from about 85 SUS to about 250 SUS at 210 F. Its molecular weight may range from about 500 to 2000 or even greater. Sulfonic acids can be obtained by the treatment of bright stock with any of the above illustrated sulfonating agents. More specific examples of useful sulfonic acids include dialkylbenzene sulfonic acids of 400 molecular weight (the alkyl group is essentially a straight chain) and monoalkyl-benzene sulfonic acids having a molecular weight of about 500 wherein the alkyl group is a branched chain alkyl group.

The sulfonic acids which can be treated in accordance with the process of the present invention also may be derived by the reacidification of various metal salts of sulfonic acids, and particularly reacidification with sulfuric acid. Such reacidified sulfonic acids may be initially washed with water to remove most of the inorganic salts formed in the reacidification process prior to treatment in accordance with the process of the present invention. In accordance with the present invention, the concentration of any low equivalent weight organic sulfonic acids present in the original metal salts can be reduced to more desirable levels.

In the present process, the organic sulfonic acid compositions ("acid mass") are treated with ammonia in the presence of water to neutralize the acids in said acid mass and to form ammonium salts of said acids. The ammonia utilized in this step may be anhydrous ammonia, aqueous ammonia, or mixtures thereof. Naturally, this anhydrous ammonia does not have to be completely anhydrous and may contain various amounts of moisture since water is present in this step in any event. When anyhdrous ammonia is utilized, it is generally utilized in gaseous form and is merely bubbled below the surface of the mass. When aqueous ammonia is utilized, the aqueous ammonia preferably is mixed with the water and the acid is added to said mixture.

The amount of ammonia added to the mixture should be sufficient to neutralize substantially all of the inorganic sulfur acid contaminants present and substantially all of the organic sulfonic acids. When all of the ammonia has been added, the mixture is agitated for a period of time sufficient to effect neutralization and to convert the acids to their ammonium salts.

The amount of water included in the mixture during the step of neutralization of the acid mass is not critical. Generally, however, sufficient water should be present to insure that all of the ammonia added to the reaction mixture is consumed in the salt formation or is in a form which is readily available to neutralize the remaining acid. It is desirable to have sufficient water present to prevent gaseous ammonia from leaving the neutralization reactor.

In one embodiment of the invention, all of the water to be used in the neutralization and first phase separation is included in the neutralization step. In another embodiment, additional water is added after neutralization but prior to phase separation. The former embodiment reduces the number of steps involved and helps to ensure that gaseous ammonia does not escape from the reaction vessel.

In one embodiment of the present invention, it is preferred to include an oleophilic alcohol in the mixture utilized in the first step for neutralization of the acid mass. The oleophilic alcohols whether included in the initial reaction mixture or added to the neutralized mixture prior to phase separation results in improved and unusual results when the neutralized sulfonic acid mixture is treated with additional water to effect phase separation. As will be discussed more fully below, the presence of the oleophilic compound results in improved selectivity in the water extraction steps and further results in the reduction of the level of undesirable low equivalent weight organic sulfonic acids in the product.

The preferred oleophilic alcohols are the aliphatic alcohols containing from about 5 to 8 carbon atoms such as the pentanols, hexanols and octanols. A particularly useful oleophilic alcohol is primary amyl alcohol and mixtures of alcohols containing principally primary amyl alcohol.

Following neutralization of the acid mass with ammonia, the neutralized acid mass mixture is contacted with additional water to form an aqueous phase and an organic phase. As mentioned above, the presence of an oleophilic alcohol facilitates the separation of the aqueous phase and the organic phase. It has been discovered that the oleophilic alcohol can be introduced at one or more stages of the process of the present invention so long as it is present at the time the aqueous and organic phases are being formed and separated. Thus, the oleophilic alcohol can be included in an original mixture of the acid mass and the alcohol with or without water prior to treatment with ammonia. Alternatively, the original mixture may comprise ammonia, the oleophilic alcohol and optionally water. In another alternative embodiment, the acid mass may be neutralized with ammonia followed by addition of the oleophilic alcohol prior to contacting the neutralized acid mass mixture with additional water to form the aqueous and organic phases. Although any of the above alternative procedures can be utilized, it is preferred to include the oleophilic alcohol in the original mixture prior to neutralization of the acid mass with ammonia.

The above description is a general description of the various embodiments of the present invention. The various embodiments of the invention will now be described in detail.

In one embodiment (herein referred to as "embodiment I"), the process of reducing the inorganic sulfur-containing acid and low equivalent weight organic sulfonic acid content of an acid mass comprises the steps of (a) treating the acid mass with ammonia in the presence of water and an oleophilic alcohol to neutralize the acids in said acid mass and to form a mixture containing the ammonium salts of said acids, (b) allowing separation of the mixture to provide a lower aqueous phase containing water-soluble ammonium salts and an upper phase comprising the oleophilic alcohol and ammonium salts of the organic sulfonic acids, and (c) recovering at least a portion of said upper phase.

In this embodiment, the first step comprises treating the acid mass with ammonia in the presence of water and the oleophilic alcohol to neutralize the acids in said acid mass and to form ammonium salts of said acids. The sequence in which the various components are mixed and are brought into contact with each other is not critical except that where acid corrosion is to be avoided or minimized, it is desirable to introduce the acid mass after the ammonia is introduced into the reaction mixture. Thus, a mixture of aqueous ammonia and the oleophilic alcohol can be prepared and thereafter the acid mass can be added to the mixture to effect the desired neutralization. In the above process, some or all of the aqueous ammonia may be replaced by gaseous ammonia which is added to the oleophilic alcohol or to a mixture of water and the oleophilic alcohol followed by addition of the acid mass. As mentioned previously, the amount of ammonia utilized in step (a) should be sufficient to neutralize all of the inorganic acid and organic acid components present in the acid mass. The amount of oleophilic alcohol present in step (a) may vary over a wide range and generally, the amount of oleophilic alcohol present will be sufficient to provide a weight ratio of alcohol to acid mass of at least 0.5:1, and more preferably a weight ratio of at least 1.5:1. When lesser amounts of the oleophilic alcohol are included in step (a), the ability to selectively extract inorganic and low equivalent weight organic sulfonic acids is reduced A preferred oleophilic alcohol in step (a) is primary amyl alcohol.

When the acid mass has been completely neutralized in accordance with step (a), the acid mass mixture derived from step (a) may be contacted with additional water with agitation to facilitate the formation of an aqueous phase and an organic phase. However, if sufficient water is included in step (a), it is not necessary to add water to the neutralized acid mixture. Contact between the neutralized acid mass mixture, the water, and oleophilic alcohol may be conducted at elevated temperatures up to about the boiling point of the mixture, and more generally about 65°–80° C. It has been observed with some neutralized acid mass mixtures that the formation of the two phases and the separation of the aqueous phase from the organic phase is facilitated at the more elevated temperatures.

The aqueous phase and the organic phase formed are allowed to separate to provide a lower aqueous phase containing water-soluble ammonium salts and an upper phase comprising the oleophilic alcohol and primarily the ammonium salts of the organic sulfonic acids. Depending on the relative amount of water utilized, varying amounts of the water-soluble ammonium salts may remain in the upper phase, but these can be removed by subsequent extractions with water as will be described hereinafter.

When the phases have separated sufficiently, at least a portion of the upper phase is recovered since this upper phase contains the desirable organic sulfonic acid as the ammonium salt. Because this upper phase also contains minor amounts of water-soluble inorganic salts which were not extracted in the first separation, and minor amounts of undesirable ammonium salts of lower equivalent weight sulfonic acids, the recovered upper phase may be, and is preferably, subjected to at least one additional water extraction whereby the recovered upper phase is contacted with water, the phases are allowed to separate, and the new upper phase is recovered. Although generally unnecessary, additional oleophilic alcohol may be added to the recovered upper phase prior to the subsequent extractions with water.

In the above embodiment, as well as subsequently discussed embodiments, it has been discovered that multiple extraction of the recovered upper phase is desirable and preferred for obtaining maximum selectivity and yield of the desired ammonium salt of organic sulfonic acid. Also, the selectivity and yield is increased when lesser amounts of water are used in each extraction. As mentioned above, the process of the present invention provides a means for reducing the amount of undesirable inorganic sulfur-containing acid and low equivalent weight organic sulfonic acids present in a sulfonic acid mass. The process of the present invention as illustrated by the various embodiments results in the initial removal of a significant amount of the inorganic sulfur-containing acid followed by removal of the low equivalent weight organic sulfonic acids. For example, when the recovered upper phase is subjected to four extractions with water, the water phases recovered from each of the extractions contain the inorganic and low equivalent weight organic sulfonic acid salts in differing ratios. The first water extract will contain a relatively large amount of the inorganic salt with little or no organic salt; the second water extract will contain a lesser amount of the inorganic salts but still significantly more inorganic than organic salts; the third water extract will contain primarily the low equivalent weight organic sulfonic acid salts; and the fourth water extract also will contain primarily the ammonium salt of the low equivalent weight organic acid. It generally is not possible to remove any significant quantity of the low equivalent weight organic sulfonic acid salts when only one extraction step is utilized.

Another embodiment ("embodiment II") of the process of the present invention for reducing the inorganic sulfur-containing acids and the low equivalent weight organic sulfonic acid content of an acid mass comprises the steps of (a) treating the acid mass with ammonia in the presence of water to neutralize the acids in said acid mass and to form ammonium salts of said acids, (b) contacting said neutralized acid mass mixture with additional water in the presence of an oleophilic alcohol to form an aqueous phase and an organic phase, (c) allowing separation of the phases to provide a lower aqueous phase containing water-soluble ammonium salts and an upper phase comprising the oleophilic alcohol and ammonium salts of the organic sulfonic acids, (d) recovering at least a portion of said upper phase, and (e) repeating steps (b), (c) and (d) on the upper phase recovered in step (d) at least once with the proviso that the presence of alcohol is optional when step (b) is repeated.

In this embodiment, the oleophilic alcohol does not need to be present prior to the neutralization of the acid mass mixture. The oleophilic alcohol can be added to the neutralized acid mass mixture just prior to the addition of water in step (b). This embodiment II further differs from embodiment I in that multiple extractions are an essential feature of the embodiment. The advantages and the improved results obtained from the multiple extraction has been discussed in detail above and is equally applicable to embodiment II.

Another embodiment (embodiment III) of the invention for reducing the inorganic sulfur-containing acid and the low equivalent weight organic sulfonic acid content of an acid mass is illustrated by the following process which comprises the steps of (a) treating the acid mass with ammonia in the presence of water to neutralize the acids in said acid mass and to form ammonium salts of said acids, (b) contacting said neutralized acid mass mixture with additional water in the presence of an oleophilic alcohol wherein the amount of alcohol present provides a weight ratio of alcohol to acid mass of at least 1.5:1 to form an aqueous phase and an organic phase, (c) allowing separation of the phases to provide a lower aqueous phase containing water-soluble ammonium salts and an upper phase comprising the oleophilic alcohol and ammonium salts of the organic sulfonic acids, (d) recovering at least a portion of said upper phase. This embodiment is similar to embodiment II except that the minimum amount of oleophilic alcohol present must be sufficient to provide a weight ratio of alcohol to acid mass of at least 1.5:1, and multiple extractions are not required in embodiment III, but are only optional. Embodiment III differs from embodiment I in that the oleophilic alcohol can be introduced into the process either prior to, during, or after neutralization with ammonia. However, the amount of alcohol utilized in embodiment III must provide a weight ratio of alcohol to acid mass of at least 1.5:1 wherein lesser ratios can be utilized in embodiment I.

With respect to the remaining features, process conditions etc. of embodiments II and III, the discussion above with respect to embodiment I is applicable. Thus, for example, the separation step (c) in both embodiments II and III is facilitated when the separation is allowed to proceed at an elevated temperature of up to about the boiling point of the mixture. Similarly, the discussion regarding the relative amount of water, acid, alcohol and ammonia is applicable to all three embodiments.

The upper phases recovered in the final steps of the process of the invention as illustrated in embodiments I, II and III can be used as obtained or the liquid upper phase can be treated to remove low boiling materials such as the oleophilic alcohols and water. Generally, such low boiling materials will be removed by heating the liquid phase to an elevated temperature to drive off the alcohol and/or water. Obviously, the removal of the low boiling materials can be conducted either at atmospheric or at reduced pressures.

As mentioned previously, the upper phase recovered in the final step of the various embodiments of the process of this invention contains, as the active chemical compound, organic sulfonic acid salts and possibly free organic sulfonic acids. In another preferred embodiment, the organic sulfonic acid ammonium salts which have been treated in accordance with the process of the invention to reduce the concentration of undesirable inorganic sulfonic acid salts and undesirable low equivalent weight organic sulfonic acids (e.g., disulfonic acids), can be converted to useful metal sulfonates, and more particularly oil-soluble metal sulfonates by reacting said ammonium salts with at least one basically reacting metal compound in such amounts and under such conditions as to form metal salts of said organic sulfonic acids. The basically reacting metal compounds which may be employed in accordance with this invention are exemplified by the oxides, hydroxides and carbonates of the monovalent and polyvalent metals. The monovalent metals are sodium, potassium and lithium. The polyvalent metals include calcium, magnesium, strontium, barium, zinc, aluminum, lead, copper, tin, chromium, cobalt, cadmium, etc. Preference generally is given for polyvalent metals, with special preference given the alkaline earth metal group which consists of calcium, magnesium, strontium and barium.

When the ammonium salts prepared and treated in accordance with the process of the present invention are reacted with at least one basically reacting metal compound, metal salts are obtained which may be categorized as being either neutral metal salts or basic metal salts. Basic metal salts contain metal in amounts that are in excess, frequently substantially in excess, of those equivalent to the equivalents of sulfonic acid present. The term "metal ratio" often is used to define the quantity of metal in these basic salts relative to the quantity of sulfonic acid, and is defined herein as the ratio of the number of equivalents of metal to the number of equivalents thereof which would be present in a normal salt based upon the usual stoichiometry of the compounds involved. Compounds having high metal ratios, i.e., substantial excess of metal, also have been referred to in the art by name such as "complex", "superbased", and "overbased" salts, and the method for their preparation commonly is referred to as "overbasing".

The neutral metal salts can be prepared by well known techniques of reacting the ammonium salts of the organic sulfonic acids prepared in accordance with the present invention with an equivalent amount of the basically reacting metal compounds.

The commonly employed methods for preparing the basic salts involve heating a mineral oil solution of the acid with a stoichiometric excess of the basically reacting metal compound at a temperature generally above 50° C. followed by filtration of the resulting mass. The use of a "promoter" in the preparation of the basic salts to aid in the incorporation of large excesses of metal likewise is known. Examples of compounds useful as the promoter include phenolic substances such as phenol, napthol, alkylphenol, thiophenol, sulfurized alkylphenol and condensation products of formaldehyde with a phenolic substance; alcohols such as methanol, 2-propanol, octyl alcohol, Cellosolve, Carbitol, ethylene glycol, stearyl alcohol, and cyclohexyl alcohol; and amines such as aniline, phenoline diamine, phenothiazine and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

In the preparation of high metal ratio products using promoters, an excess of the metal base is added to the ammonium salt of the sulfonic acid together with promoter and water. The resulting mixture is heated with agitation and the product dried by heating for a short time at about 150° C. to yield the desired basic metal sulfonate. Optionally, the product can be filtered if desired.

In another method of preparing overbased metal sulfonates, the mixture of ammonium salt of the organic sulfonic acid, mineral oil, promoter and basic metal oxide is heated to an elevated temperature to form a neutral metal salt, and after removing the ammonia, an inorganic acidic material such as carbon dioxide is introduced into the process mass to promote the formation of an overbased metal sulfonate.

A substantial amount of the acid material must be employed in the process, generally, enough to substantially reduce the titratable basicity of the mass, and usually an amount sufficient to substantially neutralize the mass.

The temperature of the reaction should be sufficiently elevated to cause the reaction of the ammonium salts and the basic metal compounds with the liberation and driving off of ammonia, and replacement by the metal. This generally is accomplished at temperatures between about 50° C. and 200° C., and preferably between 50° C. and 110° C.

In one preferred mode of operation, the basic metal compound is added in small portions to the ammonium organic sulfonate. When all of the basic metal compound has been added, the mixture is heated for an additional period of time usually from about 0.5 to about 2 hours or more.

Procedures for converting the ammonium salt of the organic sulfonic acid prepared in accordance with this invention to neutral and basic metal salts are well known in the art. Examples of patents describing processes for preparing highly basic metal sulfonates include U.S. Pat. Nos. 2,760,970; 3,488,284; 3,539,511; 3,544,463; and 3,629,109. The disclosures of these patents are incorporated by reference herein for their disclosures of the preparation of basic metal salts of sulfonic acids.

The basic metal salts prepared in accordance with the present invention results in the formation of highly basic organic sulfonate salts exhibiting satisfactory viscosity properties. It has been discovered that the removal of the undesirable components from the crude acid mass enables the preparation of highly basic materials exhibiting useful viscosities whereas the preparation of highly basic materials from the crude acid mass results in highly viscous materials which must be posttreated, such as with water, to reduce the viscosity to acceptable levels. Also, the highly basic materials prepared in accordance with the procedure of the invention contain lower contents of gel-like and insoluble materials.

The basic metal salts prepared in accordance with the process of the invention are useful primarily as additives for lubricating oils and normally liquid fuels and can be employed in the same manner as known basic salts of the prior art such as described in U.S. Pat. Nos. 2,585,520; 2,739,124; 2,895,913; 3,149,074; 3,150,089; and 2,325,494. In lubricants, such as crankcase lubricating oils, the basic metal salts of the invention function as detergents that promote engine cleanliness reduce wear mainly by neutralizing acidic products such as those formed by the oxidation of the other components during combustion.

The basic metal salts prepared in accordance with the present invention can be employed in the variety of lubricants based on diverse oils of lubricating viscosity.

They can be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic transmission fluids, transaxle lubricants, gear lubricants, metal-working lubricants, hydraulic fluids and other lubricating oil and grease compositions can also benefit from the incorporation therein of the basic metal salts of the invention.

Natural oils include animal oils and vegetable oils (e.g., castor, lard oil) liquid petroleum oils and hydrorefined, solvent-treated or acid-treated mineral lubricating oils of the paraffinic, naphthenic and mixed paraffinic-naphthenic types. Oils of lubricating viscosity derived from coal or shale are also useful base oils.

Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, poly(1-hexenes), poly(1-octenes), poly(1-decenes)); alkylbenzenes (e.g., dodecylbenzenes, tetradecylbenzenes, dinonylbenzenes, di(2-ethylhexyl)benzenes; polyphenyls (e.g., biphenyls, terphenyls, alkylated polyphenols); and alkylated diphenyl ethers and alkylated diphenyl sulfides and the derivatives, analogs and homologs thereof.

Alkylene oxide polymers and interpolymers and derivatives thereof where the terminal hydroxyl groups have been modified by esterification, etherification, etc., constitute another class of known synthetic lubricating oils. These are exemplified by polyoxyalkylene polymers prepared by polymerization of ethylene oxide or propylene oxide, the alkyl and aryl ethers of these polyoxyalkylene polymers (e.g., methyl-polyisopropylene glycol ether having an average molecular weight of 1000, diphenyl ether of poly-ethylene glycol having a molecular weight of 500–1000, diethyl ether of polypropylene glycol having a molecular weight of 1000–1500); and mono- and polycarboxylic esters thereof, for example, the acetic acid esters, mixed $C_3$–$C_8$ fatty acid esters and $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol and tripentaerythritol.

Silicon-based oils such as the polyalkyl-, polyaryl-, polyalkoxy-, or polyaryloxysiloxane oils and silicate oils comprise another useful class of synthetic lubricants; they include tetraethyl silicate, tetraisopropyl silicate, tetra-(2-ethylhexyl) silicate, tetra-(4-methyl-2-ethylhexyl) silicate, tetra-(p-tert-butylphenyl) silicate, hexa-(4-methyl-2-pentoxy)disiloxane, poly(methyl)siloxanes and poly(methylphenyl) siloxanes. Other synthetic lubricating oils include liquid esters of phosphorus-containing acids (e.g, tricresyl phosphate, trioctyl phosphate, diethyl ester of decylphosphonic acid) and polymeric tetrahydrofurans.

Unrefined, refined and rerefined oils can be used in the lubricants of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques, such as distillation, solvent extraction, acid or base extraction, filtration and percolation are known to those skilled in the art. Rerefined oils are obtained by processes similar to those used to obtain refined oils applied to refined oils which have been already used in service. Such rerefined oils are also known as reclaimed or reprocessed oils and often are additionally processed by techniques for removal of spent additives and oil breakdown products.

Generally the lubricants of the present invention contain a lubricating improving amount of one or more of the basic metal salts of this invention, e.g., sufficient to provide it with improved detergent/dispersant properties. Normally the amount employed will be about 0.05% to about 20%, preferably about 0.1% to about 10% of the total weight of the lubricating composition. This amount is exclusive of solvent/diluent medium. In lubricating compositions operated under extremely adverse conditions, such as lubricating compositions for marine diesel engines, the metal salts of this invention may be present in amounts of up to about 30% by weight, or more, of the total weight of the lubricating composition.

The invention also contemplates the use of other additives in combination with the basic metal salts compositions of this invention. Such additives include, for example, other detergents and dispersants of the ash-producing or ashless type, corrosion- and oxidation-inhibiting agents, pour point depressing agents, extreme pressure agents, antiwear agents, color stabilizers and anti-foam agents.

The other ash-producing detergents (in addition to the basic metal salts of the invention) are exemplified by oil-soluble neutral and basic salts of alkali or alkaline earth metals with carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

Ashless detergents and dispersants are so-called despite the fact that, depending on its constitution, the dispersant may upon combustion yield a nonvolatile material such as boric oxide or phosphorus pentoxide; however, it does not ordinarily contain metal and therefore does not yield a metal-containing ash on combustion. Many types are known in the art, and any of them are suitable for use in the lubricant compositions of this invention. The following are illustrative:

(1) Reaction products of carboxylic acids (or derivatives thereof) containing at least about 30 and preferably at least about 50 carbon atoms with nitrogen containing compounds such as amine, organic hydroxy compounds such as phenols and alcohols, and/or basic inorganic materials. Examples of these "carboxylic dispersants" are described in British Pat. No. 1,306,529 and in many U.S. patents including the following:
  3,163,603
  3,184,474
  3,351,552
  3,381,022
  3,541,012
  3,543,678

(2) Reaction products of relatively high molecular weight aliphatic or alicyclic halides with amines, preferably polyalkylene polyamines. These may be characterized as "amine dispersants" and examples thereof are described for example, in the following U.S. patents:
  3,275,554
  3,438,757
  3,454,555
  3,565,804

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. patents are illustrative:
  2,459,112
  2,962,442
  3,442,808
  3,448,047
  3,591,598
  3,600,372

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. patents:
  3,036,003
  3,087,936
  3,282,955
  3,312,619
  3,639,242
  3,502,677

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-subsituted acrylates. These may be characterized as "polymeric dispersants" and examples thereof are disclosed in the following U.S. patents:
  3,329,658
  3,449,250
  3,519,565
  3,666,730
  3,687,849
  3,702,300

The above-noted patents are incorporated by reference herein for their disclosures of ashless dispersants.

Extreme pressure agents and corrosion- and oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate, phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl napthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)-phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

Many of the above-mentioned extreme pressure agents and corrosion-oxidation inhibitors also serve as antiwear agents. Zinc dialkylphosphorodithioates are a well known example.

Pour point depressants are a particularly useful type of additive often included in the lubricating oils described herein. The use of such pour point depressants in oil-based compositions to improve low temperature properties of oil-based compositions is well known in the art. See, for example, page 8 of "Lubricant Additives" by C. V. Smalheer and R. Kennedy Smith (Lezius-Hiles Co. publishers, Cleveland, Ohio, 1967).

Examples of useful pour point depressants are polymethacrylates, polyacrylates; polyacrylamides; condensation products of haloparaffin waxes and aromatic compounds; vinyl carboxylate polymers; and terpolymers of dialkylfumarates, vinylesters of fatty acids and alkylvinylethers. Pour point depressants useful for the purposes of this invention, techniques for their preparation and their uses are described in U.S. Pat. Nos. 2,387,501; 2,015,748; 2,655,479; 1,815,022; 2,191,498; 2,666,746; 2,721,877; 2,721,878; and 3,250,715 which are hereby incorporated by reference for their relevant disclosures.

Anti-foam agents are used to reduce or prevent the formation of stable foam. Typical anti-foam agents include silicones or organic polymers. Additional anti-foam compositions are described in "Foam Control Agents", by Henry T. Kerner (Noyes Data Corporation, 1976), pages 125–162.

The basic metal salt compositions of this invention can be added directly to the lubricant. Preferably, however, they are diluted with a substantially inert, normally liquid organic diluent such as mineral oil, naphtha, benzene, toluene or xylene, to form an additive concentrate. These concentrates usually contain from about 1% to 90% by weight of the basic metal salt of this invention and may contain, in addition, one or more other additives known in the art or described hereinabove. The remainder of the concentrate is the substantially inert normally liquid diluent.

When used as fuel additives, the basic metal salts of the invention will be employed in amounts which are affected to provide the desired results. When employed in normally liquid petroleum distillate fuels such as fuel oils, diesel fuels, gasolines, aviation gasoline, aviation jet fuels, etc., they promote engine cleanliness, particularly of the fuel systems such as fuel lines, carburetors, injectors, pumps and the like. In furnace fuel oils, for example, the metal salts of the invention serve as anti-screen clogging agents. Furthermore, diesel fuels and other fuels which tend to use black exhaust smoke in diesel engines, the basic metal salts are pressed to formation and evolution of these black exhaust smokes. Likewise, the basic metal salts of the invention can be employed as vanadium scavengers in furnaces and other devices which burn residual fuel oils.

It is contemplated that the basic metal salts of the invention will be employed in fuels in combination with other conventional fuel additives such as de-icers, anti-knock agents, other smoke suppressants, and the like. When the basic metal salts are prepared for use in fuels according to the process of the present invention, it is sometimes desirable to use non-mineral oil diluents exclusively (e.g, xylene, toluene, heptene, naphtha or other such diluents as described hereinbefore) and to retain the basic metal salts produced as solutions in these diluents. Of course, combinations of these non-mineral oil diluents and mineral oil can be used in the processes of the invention.

The following examples illustrate the processes of the invention and the various embodiments. Unless otherwise indicated, all parts and percentages used in the specification and claims are by weight, and all temperatures are in degrees centigrade.

EXAMPLE 1

Ammonium Salt

In this example, a bright stock sulfonic acid is used which is obtained by sulfonation of about 1000 parts of a bright stock having a molecular weight of about with sulfur trioxide derived from about 117 parts of 65% oleum. The sulfonic acid prepared in this manner is a direct acid number of 60.5 and contains 3% sulfur.

About 1200 parts of the above-described sulfonic acid are charged to a glass-lined reactor equipped with reflux column and agitator. To the reactor, there is added about 1707 parts of amyl alcohol (recovered distillate from a previous procedure containing about 5.6% water), and 693 parts of fresh amyl alcohol with stirring. To this mixture there is added 100 parts of aqueous ammonia (27–29% ammonia) over a period of 10 minutes at a temperature of about 45°–50° C. The exotherm of this reaction is mild, but the materials should not be allowed to exceed a temperature of 75°–80° C. The mixture is basic to pH paper.

Additional water (384 parts) is added to the reactor and mixed for 10 minutes. The material then is allowed to settle 3 hours holding the batch temperature at about 70°–75° C. The lower aqueous phase is removed from the reactor. The material which remains in the reactor (the upper phase) is treated with 300 parts of water with mixing for a period of about 10 minutes. The material then is allowed to settle for 3 hours at 70°–75° C., and the lower aqueous phase is removed. The material remaining in the reactor (upper phase) is dried to a temperature of about 150° C. over a period of 15 hours to remove water and some of the amyl alcohol. The residue is the desired ammonium salt containing some amyl alcohol.

The aqueous phase recovered from the two extraction procedures is analyzed, and the results are summarized in the following Table I.

|  | First Extraction | Second Extraction |
|---|---|---|
| % Water | 80.1 | 71.0 |
| % Amyl Alcohol | 1.8 | 8.9 |
| % Ammonium Sulfate/Sulfite | 18.1 | 2.5 |
| % Organic | Nil | 17.6 |

EXAMPLE 2

Conversion of Ammonium Sulfonate to Calcium Sulfonate

In this example, the extracted ammonia salt obtained in Example 1 is converted to an essentially neutral calcium salt.

Blending oil (160 parts) is charged to a reactor equipped with agitator, column, condenser, receiver and circulating systems. Water (2.6 parts) and 10 parts of calcium hydroxide are added to the reactor followed by the addition of 456 parts of the ammonium salt prepared in Example 1. The addition of the ammonium salt is made over a period of about 2 hours whereupon the temperature rises to about 60° C. The mixture contained in the reactor is heated to about 150° C. over a period of 5 hours whereupon ammonia is liberated and removed from the system. At or below a temperature of 150° C., low boiling liquids also are distilled which comprise water and some amyl alcohol.

In order to remove additional low boiling materials, the mixture in the reactor is blown with nitrogen at a rate of about 5 pounds per hour at a temperature of about 150° C. The nitrogen blowing is continued for about 6 hours during which time additional amyl alcohol distillate is recovered. The residue is cooled to about 60° C. The residue is the desired neutral calcium salt of the organic sulfonic acid. Analysis of this residue indicates a calcium content of 0.99% and a sulfur content of 1.30%.

EXAMPLE 3

Basic Calcium Sulfonate

In this example, the neutral calcium sulfonate prepared in Example 2 is converted to a basic calcium sulfonate containing 11.2% calcium and having a 300 total base number.

A solution of 26 parts of methanol and 1.4 parts of calcium chloride is prepared and added to a reactor which contains 595 parts of the dried neutral calcium sulfonate prepared in Example 2. To this mixture there is added 4 parts of water, 46 parts of a reaction product of heptyl phenol with formaldehyde further partially reacted (80% conversion) with calcium hydroxide, and 69 parts of an isobutyl/amyl alcohol mixture (60/40 mole %). The order of addition is not critical. The temperature is adjusted to about 60°-65° C. Calcium hydroxide (55 parts) is added to the reactor and the mixture agitated for 10 minutes whereupon the mixture is treated with carbon dioxide at a rate of about 4.6 parts per hour by way of a submerged lime. The first increment of carbonation is continued for 3 hours and 10 minutes at about 60°-65° C. Analysis at the end of the carbonation of the first increment of lime addition indicates a volume solids content of 6.8% and a DBN of 48.

Five additional increments of calcium hydroxide are made and carbonated in a manner described above. Analysis at the end of the last carbonation indicates a volume solids content of 6.8% and a DBN of 47. The reaction product is flash stripped through a heat exchanger to a receiving tank over a period of 2.2 hours at a temperature of about 150° C. The system pressure is lowered to 50 mm. Hg. (abs) over 30 minutes and maintained for an additional 30 minutes at about 150° C., and the reaction product is filtered. The filtrate is the desired overbased calcium sulfonate.

We claim:

1. A sulfonic acid composition prepared by the process comprised of:
    reacting a sulfonatable organic compound with a sulfonating agent to form an acid mass comprising organic sulfonic acid and inorganic sulfonic acid;
    allowing the acid mass to separate into an upper organic sulfonic acid layer and a lower acid sludge layer;
    isolating the upper organic sulfonic acid layer;
    treating the upper organic sulfonic acid layer with ammonia in the presence of water and an oleophilic alcohol selected from the group consisting of amyl alcohols and hexanols to neutralize the acids and to form a mixture containing ammonium salts of the acids;
    allowing separation of the mixture to provide a first lower aqueous phase containing water-soluble ammonium salts and a first upper phase comprising the oleophilic alcohols and ammonium salts of the organic sulfonic acids; and
    recovering the first upper phase of oleophilic alcohols and ammonium salts.

2. The sulfonic acid composition prepared by the process as claimed in claim 1, further comprising:
    adding water to the recovered first upper phase of oleophilic alcohols and ammonium salts;
    allowing separation to provide a second lower aqueous phase and a second upper phase; and
    recovering the second upper phase.

3. The sulfonic acid composition prepared by the process as claimed in claim 2, wherein the weight ratio of the oleophilic alcohols to the acid mass is at least 0.5:1.

4. The sulfonic acid composition as claimed in claim 3, wherein the weight ratio of oleophilic alcohols to acid mass is at least 1.5:1.

5. The sulfonic acid composition as claimed in claim 2, wherein the oleophilic alcohols further comprises any alphatic alcohol containing about 5-8 carbon atoms.

6. The sulfonic acid composition as claimed in claim 4, wherein the oleophilic alcohol is a mixture of alcohols containing principally primary amyl alcohol.

7. The sulfonic acid composition as claimed in claim 6, wherein the sulfonatable organic compound is an aromatic hydrocarbon compound and the sulfonating agent is selected from the group consisting of oleum, sulfuric acid, chlorosulfuric acid, and sulfur trioxide.

8. The sulfonic acid composition as claimed in claim 1, wherein the reacting of the sulfonatable organic compound with the sulfonating agent is carried out at a temperature in the range from about 25° C. to about 75° C. for a period of time in the range of about 15-20 minutes.

9. The sulfonic acid composition as claimed in claim 1, wherein the ammonia treating the upper organic sulfonic acid layer is added in an amount sufficient to neutralize substantially all acids contained in the upper organic sulfonic acid layer.

10. An additive concentrate for lubricating oils and normally liquid fuels comprising a substantially inert, normally liquid organic diluent and a sulfonic acid composition prepared by the steps comprising:
    reacting a sulfonatable organic compound with a sulfonating agent to form an acid mass comprising organic sulfonic acid and inorganic sulfonic acid;
    allowing the acid mass to separate into an upper organic sulfonic acid layer and a lower acid sludge layer;
    isolating the upper organic sulfonic acid layer;
    treating the upper organic sulfonic acid layer with ammonia in the presence of water and an oleophilic alcohol selected from the group consisting of amyl alcohols and hexanols to neutralize the acids and to form a mixture containing ammonium salts of the acids;
    allowing separation of the mixture to provide a first lower aqueous phase containing water-soluble ammonium salts and a first upper phase comprising the oleophilic alcohols and ammonium salts of the organic sulfonic acids; and
    recovering the first upper phase of oleophilic alcohols and ammonium salts.

11. A lubricant comprising a major amount of an oil of lubricating viscosity and a minor amount of a sulfonic acid composition prepared by the steps comprising:
    reacting a sulfonatable organic compound with a sulfonating agent to form an acid mass comprising organic sulfonic acid and inorganic sulfonic acid;
    allowing the acid mass to separate into an upper organic sulfonic acid layer and a lower acid sludge layer;
    isolating the upper organic sulfonic acid layer;
    treating the upper organic sulfonic acid layer with ammonia selected from the group consisting of amyl alcohols and hexanols to neutralize the acids and to form a mixture containing ammonium salts of the acids;

allowing separation of the mixture to provide a first lower aqueous phase containing water-soluble ammonium salts and a first upper phase comprising the oleophilic alcohols and ammonium salts of the organic sulfonic acids;

recovering the first upper phase of oleophilic alcohols and ammonium salt;

adding water to the recovered upper phase of oleophilic alcohols and ammonium salts;

allowing separation to provide a second layer aqueous phase and a second upper phase; and recovering the second upper phase.

12. A functional fluid, comprising a major amount of a lubricating oil and a minor amount of the additive concentrate of claim 10.

* * * * *